US006828467B2

(12) United States Patent
Miura et al.

(10) Patent No.: US 6,828,467 B2
(45) Date of Patent: Dec. 7, 2004

(54) PROCESS FOR PRODUCING FLUORINATED METHYL-BENZYL ALCOHOL

(75) Inventors: Motoo Miura, Tokyo (JP); Yuseki Suyama, Kawasaki (JP); Kohei Morikawa, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/380,047

(22) PCT Filed: Sep. 26, 2001

(86) PCT No.: PCT/JP01/08355
§ 371 (c)(1),
(2), (4) Date: Mar. 11, 2003

(87) PCT Pub. No.: WO02/26678
PCT Pub. Date: Apr. 4, 2002

(65) Prior Publication Data
US 2004/0010167 A1 Jan. 15, 2004

Related U.S. Application Data
(60) Provisional application No. 60/256,918, filed on Dec. 21, 2000.

(51) Int. Cl.$^7$ .............................................. C07C 33/46
(52) U.S. Cl. ....................................................... 568/812
(58) Field of Search ................................. 568/812, 814

(56) References Cited

U.S. PATENT DOCUMENTS 3,029,290 A * 4/1962 Roland et al. ............... 568/811
4,853,414 A * 8/1989 Robson et al. ............... 514/531
6,624,336 B1 * 9/2003 Sasaki et al. ................ 568/812

FOREIGN PATENT DOCUMENTS

| DE | 37 14 602 A | 11/1988 |
| GB | 2 127 013 A | 4/1984 |
| GB | 2 155 464 A | 9/1985 |

* cited by examiner

Primary Examiner—Michael L. Shippen
(74) Attorney, Agent, or Firm—Sughrue Mion, PLLC

(57) ABSTRACT

An object of the present invention is to provide a process for producing a fluorinated methyl-benzyl alcohol, which process is industrially applicable. A process for producing a fluorinated methyl-benzyl alcohol according to the present invention includes hydrogenolysis of one hydroxyl group in fluorinated benzene dimethanol. The hydrogenolysis can be carried out in a solvent in the presence of a catalyst. The catalyst can include at least one metal selected from cobalt, iron, copper, nickel, platinum, palladium, and rhenium, and the hydrogenolysis can be carried out using hydrogen.

14 Claims, No Drawings

PROCESS FOR PRODUCING FLUORINATED METHYL-BENZYL ALCOHOL

CROSS REFERENCE OF RELATED APPLICATION

This application is a 371 of PCT/SP01/08355 filed Sep. 26, 2001, an application filed under 35 U.S.C. §111(a) claiming benefit pursuant to 35 U.S.C. §119(e) of the filing date of Provisional Application No. 60/256,918 filed on Dec. 21, 2000, pursuant to 35 U.S.C. §111(b).

DETAILED DESCRIPTION OF THE INVENTION

1. Technical Field

The present invention relates to a process for producing fluorinated methyl-benzyl alcohols by hydrogenolysis of one hydroxyl group in a fluorinated benzene dimethanol, particularly by hydrogenolysis in a solvent in the presence of a catalyst. Fluorinated methyl-benzyl alcohols are useful as a starting material or an intermediate of medical and pharmaceutical products, agricultural chemicals or other organic compounds. For example, JP-B-1-20143/1989 discloses that fluorinated methyl-benzyl alcohols are reacted with cyclopropane carboxylic acids to obtain ethers having high insecticidal activities.

2. Background Art

For example, the following processes are proposed as the process for producing fluorinated methyl-benzyl alcohols.

1) JP-B-4-6694/1992 discloses a process for producing 4-methyl-2,3,5,6-tetrafluorobenzyl alcohol by reducing 4-methyl-2,3,5,6-tetrafluorobenzoic acid with lithium aluminum hydride in dried ether, and a process for producing 3-methyl-2,4,5,6-tetrafluorobenzyl alcohol by reducing 3-methyl-2,4,5,6-tetrafluorobenzaldehyde with sodium borohydride in methanol.

2) JP-A-63-77829/1988 discloses a process for producing 2-methyl-3,4,5,6-tetrafluorobenzyl alcohol by allowing pentafluorobenzyl alcohol to react with magnesium methyl bromide in tetrahydrofurane.

3) DE-B-3714602 discloses a process for producing 4-methyl-2,3,5,6-tetrafluorobenzyl alcohol by reducing 4-methyl-2,3,5,6-tetrafluoro benzoic acid with sodium borohydride in 1,2-dimethoxyethane.

4) GB-B-2155464 discloses a process for producing 4-methyl-2,3,5,6-tetrafluorobenzyl alcohol by reducing 4-methyl-2,3,5,6-tetrafluorobenzoic acid chloride with sodium borohydride.

However, these processes are not favorable for carrying out industrially because of having problems in that expensive reducing agents are used and strict moisture control for these reducing agents is required.

OBJECT OF THE INVENTION

Accordingly, it is an object of the invention to provide a process for producing a fluorinated methyl-benzyl alcohol, which process can be carried out industrially.

MEANS TO SOLVE THE PROBLEMS

The present invention comprises the following subjects.

[1] A process for producing a fluorinated methyl-benzyl alcohol represented by formula (2):

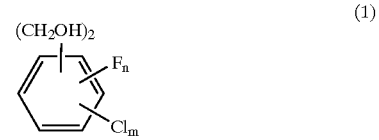

(2)

(wherein m represents an integer of 0 to 3, n represents an integer of 1 to 4, and m+n is an integer of 1 to 4), which process comprises hydrogenolysis of one hydroxyl group in a fluorinated benzene dimethanol represented by formula (1):

(1)

(wherein m and n are the same as above).

[2] The process for producing a fluorinated methyl-benzyl alcohol as described in [1], wherein the fluorinated benzene dimethanol is represented by formula (3)

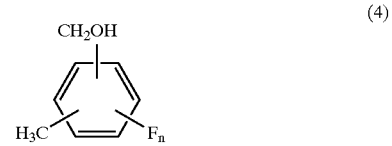

(3)

(wherein n represents an integer of 1 to 4), and the corresponding fluorinated methyl-benzyl alcohol is represented by formula (4)

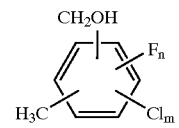

(4)

(n is the same as above).

[3] The process for producing a fluorinated methyl-benzyl alcohol as described in [1], wherein the fluorinated benzene dimethanol is tetrafluorobenzene dimethanol represented by formula (5)

(5)

and the corresponding fluorinated methyl-benzyl alcohol is tetrafluoromethyl-benzyl alcohol represented by formula (6)

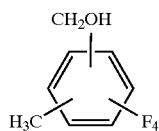

(6)

[4] The process for producing a fluorinated methyl-benzyl alcohol as described in [3], wherein the tetrafluorobenzene dimethanol of the formula (5) is 2,3,5,6-tetrafluorobenzene-1,4-dimethanol and the tetrafluoromethyl-benzyl alcohol of the formula (6) is 2,3,5,6-tetrafluoro-4-methyl-benzyl alcohol.

[5] The process for producing a fluorinated methyl-benzyl alcohol as described in any one of [1] to [4], wherein the hydrogenolysis is carried out in a solvent in the presence of a catalyst.

[6] The process for producing a fluorinated methyl-benzyl alcohol as described in [5], wherein the catalyst comprises at least one metal selected from cobalt, iron, copper, nickel, platinum, palladium and rhenium, and the hydrogenolysis is carried out using hydrogen.

[7] The process for producing a fluorinated methyl-benzyl alcohol as described in [6], wherein the catalyst is at least one catalyst selected from the group consisting of a sponge cobalt catalyst, a modified sponge cobalt catalyst, a sponge nickel catalyst and a modified sponge nickel catalyst.

[8] The process for producing a fluorinated methyl-benzyl alcohol as described in [6], wherein the catalyst is a sponge cobalt catalyst or a modified sponge cobalt catalyst.

[9] The process for producing a fluorinated methyl-benzyl alcohol as described in [6], wherein the catalyst is a supported cobalt catalyst, a supported nickel catalyst, a supported palladium catalyst or a supported rhenium catalyst.

[10] The process for producing a fluorinated methyl-benzyl alcohol as described in any one of [5] to [9], wherein the solvent is a single or mixed solvent comprising at least one selected from saturated aliphatic or alicyclic hydrocarbon, aromatic hydrocarbon, alcoholic solvent, ether of aliphatic or alicyclic hydrocarbon and water.

[11] The process for producing a fluorinated methyl-benzyl alcohol as described in [10], wherein the solvent is a single or mixed solvent comprising at least one selected from toluene, xylene, methanol, ethanol, dioxane, dioxolane and water.

[12] The process for producing a fluorinated methyl-benzyl alcohol as described in any one of [1] to [11], wherein the hydrogenolysis reaction is carried out in a hydrogen partial pressure of from 0.05 to 15 MPa.

[13] The process for producing a fluorinated methyl-benzyl alcohol as described in any one of [5] to [12], wherein the amount of the solvent used in the hydrogenolysis reaction is 1 to 20 times by mass based on the fluorinated benzene dimethanol.

[14] The process for producing a fluorinated methyl-benzyl alcohol as described in any one of [6] to [13], wherein the amount of hydrogen used in the hydrogenolysis reaction is 100 to 180% by mole based on the fluorinated benzene dimethanol.

MODE FOR CARRYING OUT THE INVENTION

The present invention is described in detail below.

The present invention relates to a process for producing fluorinated methyl-benzyl alcohols by hydrogenolysis of one hydroxyl group in fluorinated benzene dimethanol, particularly, hydrogenolysis in a solvent in the presence of a catalyst.

The fluorinated benzene dimethanol used as a starting material in the invention can be synthesized by known methods. For example, tetrafluorobenzene dimethanol can be easily prepared by hydrolysis of 2,3,5,6-tetrafluorobenzene dimethanol diacetate, as described in JP-A-1-238555/1989.

As the catalyst used in the invention, metal catalysts are favorable, particularly, a catalyst comprising at least one metal selected from cobalt, iron, copper, nickel, platinum, palladium and rhenium is more favorable.

The catalyst used may be a metal itself, a sponge metal catalyst or a supported catalyst.

The "sponge metal catalyst" used in the present invention is a porous metal catalyst obtainable from an alloy which comprises a metal insoluble in alkali or acid such as nickel or cobalt, and a metal soluble in alkali or acid such as aluminum, silicon, zinc or magnesium to thereby eluting a metal soluble in alkali or acid by use of alkali or acid.

In the present invention, it is preferred to use the sponge cobalt catalyst and sponge nickel catalyst.

Further, a modified sponge metal catalyst obtainable by modification in the presence of a metal other than nickel or cobalt, or a metal oxide thereof may be used in the present invention. Examples thereof may include a modified sponge nickel catalyst modified with molybdenum and a modified sponge cobalt catalyst modified with manganese.

The "supported catalyst" used in the present invention is a catalyst supporting a highly dispersed fine divided metal containing at least one metal species or metal oxide particles on a carrier such as silica, alumina, silica alumina, activated charcoal or diatomaceous earth.

It is preferred to use a supported cobalt catalyst, supported iron catalyst, supported copper catalyst, supported nickel catalyst, supported platinum catalyst, supported palladium catalyst and supported rhenium catalyst in the present invention.

In particular, it is preferred to use the supported cobalt catalyst, the supported nickel catalyst, the supported palladium catalyst and the supported rhenium catalyst.

Further, a supported catalyst, which comprises, as a main component, at least one metal selected from cobalt, iron, copper, nickel, platinum, palladium and rhenium, further modified by adding at least one of the above metal species or other metal species can be used in the present invention. Examples thereof may include a supported nickel-copper-alumina catalyst, supported copper-chromium-silica catalyst, supported palladium-rhenium-alumina catalyst and supported nickel-cobalt-alumina catalyst.

Next, the hydrogenolysis reaction of the invention will be described.

The amount of the catalyst added in the reaction is not particularly limited, and differs depending to the catalyst form. Generally, the catalyst is used in an amount of from 0.01 to 300% by mass, preferably 0.05 to 100% by mass, particularly preferably 0.1 to 50% by mass based on fluorinated benzene dimethanol subjected to the hydrogenolysis.

Preferable examples of the solvent used in the hydrogenolysis reaction according to the present invention may include saturated aliphatic and alicyclic hydrocarbons, aromatic hydrocarbons, alcohols, ethers of aliphatic and alicyclic hydrocarbons and water. Examples of the saturated aliphatic and alicyclic hydrocarbons include n-hexane, n-octane, iso-octane and cyclohexane; examples of the aromatic hydrocarbons include benzene, toluene and xylene; examples of alcohols include methanol, ethanol, n-propanol, isopropanol, n-butanol, ethyleneglycol and propyleneglycol; and examples of ethers aliphatic and alicyclic hydrocarbons include diethylether, diisopropylether, methyl-tertiary-butylether, tetrahydrofuran, dioxane and dioxolane. These solvents may be used singly or in a mixed one containing any of these solvents. Further, in the case of using at least two solvents as a mixed solvent, non-uniformly mixed solvents can be used. Preferable examples of the single solvent are toluene, methanol and dioxane, and preferable examples of the mixed solvent are toluene-methanol, toluene-water, toluene-methanol-water and dioxane-water. The solvent is used in an amount of from 0.5 to 30 times by mass, preferably 1 to 20 times by mass based on tetrafluorobenzene dimethanol.

The hydrogenolysis of the present invention can be carried out by introducing hydrogen into gas phase thereby heating to predetermined temperature, or by purging gas phase with inert gas that has no effect on the hydrogenolysis reaction, and heating to predetermined temperature thereby introducing hydrogen. The reaction can be carried out at a temperature of from ordinary temperature to 250° C., preferably above the temperature at which the fluorinated benzene dimethanol is melting, or dissolving in the solvent. The pressure for the hydrogenolysis reaction is appropriately from 0.05 to 15 MPa by the partial pressure of hydrogen. The hydrogen gas used in the present reaction does not have necessarily a high purity, and may contain inert gases that have no effect on the hydrogenolysis reaction especially.

The fluorinated benzene methanol used as a starting material according to the present invention is a compound represented by the above formula (1). Examples thereof may include monofluorobenzene dimethanols (such as 2-fluorobenzene-1,4-dimethanol), difluorobenzene dimethanols (such as 2,3-difluorobenzene-1,4-dimethanol, 2,5-difluorobenzene-1,4-dimethanol, 3,5-difluorobenzene-1,4-dimethanol), trifluorobenzene dimethanols (such as 2,3,5-trifluorobenzene-1,4-dimethanol), tetrafluorobenzene dimethanols (such as 3,4,5,6-tetrafluorobenzene-1,2-dimethanol, 2,4,5,6-tetrafluorobenzene-1,3-dimethanol, 2,3,5,6-tetrafluorobenzene-1,4-dimethanol), monochloro-monofluorobenzene dimethanols (such as 6-chloro-2-fluorobenzene-1,4-dimethanol), monochloro-difluorobenzene dimethanols (such as 2,3-difluoro-5-chlorobenzene-1,4-dimethanol), monochloro-trifluorobenzene dimethanols (such as 2,3,5-trifluoro-6-chlorobenzene-1,4-dimethanol), and dichloro-difluorobenzene dimethanols (such as 2,6-difluoro-4,5-dichlorobenzene-1,4-dimethanol).

Preferable examples are tetrafluorobenzene dimethanols (such as 3,4,5,6-tetrafluorobenzene-1,2-dimethanol, 2,4,5,6-tetrafluorobenzene-1,3-dimethanol, 2,3,5,6-tetrafluorobenzene-1,4-dimethanol), and a more preferable example is 2,3,5,6-tetrafluorobenzene-1,4-dimethanol.

The fluorinated methyl-benzyl alcohol obtainable by the production process of the present invention is represented by the above formula (2) and corresponds to a compound obtainable by hydrogenolysis of one hydroxy group in the fluorinated benzene dimethanol of the formula (1). Examples of the fluorinated methyl-benzyl alcohol may include preferably tetrafluoro-methyl-benzyl alcohols (such as 3,4,5,6-tetrafluoro-2-methyl-benzyl alcohol, 2,4,5,6-tetrafluoro-3-methyl-benzyl alcohol and 2,3,5,6-tetrafluoro-4-methyl-benzyl alcohol), and more preferably 2,3,5,6-tetrafluoro-4-methyl-benzyl alcohol.

The fluorinated methyl-benzyl alcohol obtained by the production process of the present invention may be purified by separating the catalyst by filtration, centrifugation and other operations, then concentration, extraction and/or distillation.

EFFECT OF THE INVENTION

According to the present invention, fluorinated methyl-benzyl alcohols, especially tetrafluoromethyl-benzyl alcohol can be produced by an industrially advantageous method.

EXAMPLES

The present invention will be described with reference to the following examples hereinafter, but it is not restricted by the examples.

Example 1

To a 1 liter autoclave, 300 ml of toluene, 25 g of a sponge cobalt catalyst in a water-containing state (in which the catalyst amount is 5 g) and 30 g of 2,3,5,6-tetrafluorobenzene-1,4-dimethanol were charged and a gas phase was thoroughly purged with hydrogen, and thereafter the hydrogen pressure was set to 1.5 MPa at ordinary temperature (the pressure means gauge pressure hereinafter). The stirring and heating for the autoclave were started and the temperature thereof was kept to 160° C. When the temperature reached to 160° C., the pressure was 2.2 MPa. The reaction was continued for 1 hr. Then, the autoclave was cooled to room temperature. After the cooling, the pressure showed 1.0 MPa. At this time, the amount of absorbed hydrogen was 104 mol % based on 2,3,5,6-tetrafluorobenzene-1,4-dimethanol charged. Hydrogen inside a reactor was removed, and thereafter the reaction mixture was recovered and the catalyst was filtered.

The reaction mixture was heated under reduced pressure to remove the solvent by distillation, and further by gradually decreasing the pressure, a fraction distilled at 665 Pas at a temperature of from 100 to 105° C. was recovered. The fraction was analyzed with nuclear magnetic resonance spectrum (NMR) analysis and gas chromatography-mass spectroscopy (GC-MS) to identify 98% 2,3,5,6-tetrafluoro-4-methyl-benzyl alcohol.

Further, using the distilled 2,3,5,6-tetrafluoro-4-methyl-benzyl alcohol as an authentic sample, a part of the reaction mixture recovered in the above reaction was analyzed with the gas chromatography internal standard method. In result, the conversion of 2,3,5,6-tetrafluorobenzene-1,4-dimethanol was 94%, the yield of 2,3,5,6-tetrafluoro-4-methyl-benzyl alcohol was 88% (on the basis of 2,3,5,6-tetrafluorobenzene-1,4-dimethanol), and the yield of 2,3,5,6-terafluoro-p-xylene was 4% (on the basis of 2,3,5,6-tetrafluorobenzene-1,4-dimethanol).

Example 2

To a 100 ml autoclave, 30 ml of 1,4-dioxane, 2.5 g of a sponge cobalt catalyst in a water-containing state (in which the catalyst amount is 0.5 g) and 3.0 g of 2,3,5,6-tetrafluorobenzene-1,4-dimethanol were charged and a gas phase was thoroughly purged with hydrogen, and thereafter the hydrogen pressure was set to 0.3 MPa at ordinary temperature. The stirring and heating for the autoclave were started and the temperature thereof was kept to 160° C. When the temperature reached to 160° C., the pressure was 0.5 MPa. Hydrogen was fed to the autoclave to keep a pressure at 0.5 MPa, and when the hydrogen absorbing amount reached to 145 mol % based on 2,3,5,6-tetrafluorobenzene-1,4-dimethanol charged while watching the hydrogen flow rate, the reaction was stopped. The reaction required 4 hr.

Then, the autoclave was cooled to room temperature. Hydrogen inside a reactor was removed, and thereafter the reaction mixture was recovered and the catalyst was filtered.

The resulting reaction mixture was analyzed with the gas chromatography internal standard method. In result, the conversion of 2,3,5,6-tetrafluorobenzene-1,4-dimethanol was 69%, the yield of 2,3,5,6-tetrafluoro-4-methyl-benzyl alcohol was 40% (on the basis of 2,3,5,6-tetrafluorobenzene-1,4-dimethanol), and the yield of 2,3,5,6-terafluoro-p-xylene was 7% (on the basis of 2,3,5,6-tetrafluorobenzene-1,4-dimethanol).

Example 3

To a 100 ml autoclave, 30 ml of 1,4-dioxane, 3.0 g of a supported palladium-carbon catalyst and 3.0 g of 2,3,5,6-tetrafluorobenzene-1,4-dimethanol were charged and a gas phase was thoroughly purged with hydrogen, and thereafter the hydrogen pressure was set to 5 MPa at ordinary temperature. The stirring and heating for the autoclave were started and the temperature thereof was kept to 220° C. When the temperature reached to 220° C., the pressure was 9 MPa. The reaction continued for 12 hr. Then, the autoclave was cooled to room temperature and the pressure after the cooling showed 4.7 MPa. At this time, the amount of absorbed hydrogen was 82 mol % based on 2,3,5,6-tetrafluorobenzene-1,4-dimethanol charged.

Hydrogen inside a reactor was removed, and thereafter the reaction mixture was recovered and the catalyst was filtered. The resulting reaction mixture was analyzed with the gas chromatography internal standard method. In result, the conversion of 2,3,5,6-tetrafluorobenzene-1,4-dimethanol was 56%, the yield of 2,3,5,6-tetrafluoro-4-methyl-benzyl alcohol was 37% (on the basis of 2,3,5,6-tetrafluorobenzene-1,4-dimethanol), and the yield of 2,3,5,6-terafluoro-p-xylene was 6% (on the basis of 2,3,5,6-tetrafluorobenzene-1,4-dimethanol).

Example 4

To a 100 ml autoclave, 30 ml of 1,4-dioxane, 1.5 g of a supported rhenium oxide-alumina catalyst and 3.0 g of 2,3,5,6-tetrafluorobenzene-1,4-dimethanol were charged and a gas phase was thoroughly purged with hydrogen, and thereafter the hydrogen pressure was set to 3 MPa at ordinary temperature. The stirring and heating for the autoclave were started and the temperature thereof was kept to 220° C. When the temperature reached to 220° C., the pressure was 4.8 MPa. The reaction continued for 5 hr.

Then, the autoclave was cooled to room temperature and the pressure after the cooling showed 2.6 MPa. At this time, the amount of absorbed hydrogen was 116 mol % based on 2,3,5,6-tetrafluorobenzene-1,4-dimethanol charged. Hydrogen inside a reactor was removed, and thereafter the reaction mixture was recovered and the catalyst was filtered. The resulting reaction mixture was analyzed with the gas chromatography internal standard method. In result, the conversion of 2,3,5,6-tetrafluorobenzene-1,4-dimethanol was 83%, the yield of 2,3,5,6-tetrafluoro-4-methyl-benzyl alcohol was 58% (on the basis of 2,3,5,6-tetrafluorobenzene-1,4-dimethanol), and the yield of 2,3,5,6-terafluoro-p-xylene was 14% (on the basis of 2,3,5,6-tetrafluorobenzene-1,4-dimethanol).

Example 5

To a 1 liter autoclave, 600 ml of toluene, 30 g of a sponge cobalt catalyst in a water-containing state (in which the catalyst amount is 6 g) and 60 g of 2,3,5,6-tetrafluorobenzene-1,4-dimethanol were charged and gas phase was thoroughly purged with nitrogen. The stirring and heating for the autoclave were started and the temperature thereof was kept to 160° C. The pressure at this time was 0.28 MPa. Hydrogen was charged to the autoclave to increase the pressure to 0.53 MPa. Then, hydrogen was further fed to the autoclave to keep the pressure at 0.53 MPa, and when the hydrogen absorbing amount reached to 130 mol % based on 2,3,5,6-tetrafluorobenzene-1,4-dimethanol charged while watching the hydrogen flow rate, the reaction was stopped. The reaction required 30 minutes.

Then, the autoclave was cooled to room temperature, gases inside the reactor were removed, and thereafter the reaction mixture was recovered and the catalyst was filtered.

The resulting reaction mixture was analyzed with the gas chromatography internal standard method. In result, the conversion of 2,3,5,6-tetrafluorobenzene-1,4-dimethanol was 99.5%, the yield of 2,3,5,6-tetrafluoro-4-methyl-benzyl alcohol was 82% (on the basis of 2,3,5,6-tetrafluorobenzene-1,4-dimethanol), and the yield of 2,3,5,6-tetrafluoro-p-xylene was 11% (on the basis of 2,3,5,6-tetrafluorobenzene-1,4-dimethanol).

What is claimed is:

1. A process for producing a fluorinated methyl-benzyl alcohol represented by formula (2):

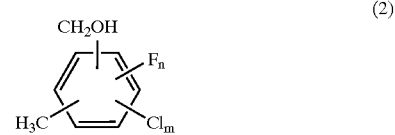

(wherein m represents an integer of 0 to 3, n represents an integer of 1 to 4, and m+n is an integer of 1 to 4), which process comprises hydrogenolysis of one hydroxyl group in a fluorinated benzene dimethanol represented by formula (1):

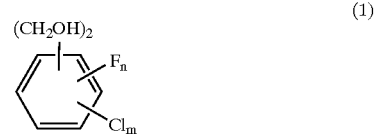

(wherein m and n are the same as above).

2. The process for producing a fluorinated methyl-benzyl alcohol according to claim 1, wherein the fluorinated benzene dimethanol is represented by the formula (3)

(wherein n represents an integer of 1 to 4), and the corresponding fluorinated methyl-benzyl alcohol is represented by formula (4):

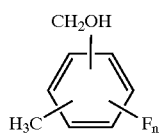

(4)

(wherein n is the same as above).

3. The process for producing a fluorinated methyl-benzyl alcohol according to claim 1, wherein the fluorinated benzene dimethanol is tetrafluorobenzene dimethanol represented by formula (5)

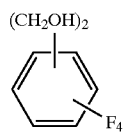

(5)

and the corresponding fluorinated methyl-benzyl alcohol is tetrafluoromethyl-benzyl alcohol represented by formula (6)

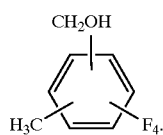

(6)

4. The process for producing a fluorinated methyl-benzyl alcohol according to claim 3, wherein the tetrafluorobenzene dimethanol of the formula (5) is 2,3,5,6-tetrafluorobenzene-1,4-dimethanol and the tetrafluoro-methyl-benzyl alcohol of the formula (6) is 2,3,5,6-tetrafluoro-4-methyl-benzyl alcohol.

5. The process for producing a fluorinated methyl-benzyl alcohol according to any one of claims 1 to 4, wherein hydrogenolysis is carried out in a solvent in the presence of a catalyst.

6. The process for producing a fluorinated methyl-benzyl alcohol according to claim 5, wherein the catalyst comprises at least one metal selected from cobalt, iron, copper, nickel, platinum, palladium and rhenium, and hydrogenolysis is carried out using hydrogen.

7. The process for producing a fluorinated methyl-benzyl alcohol according to claim 6, wherein the catalyst is at least one catalyst selected from the group consisting of a sponge cobalt catalyst, a modified sponge cobalt catalyst, a sponge nickel catalyst and a modified sponge nickel catalyst.

8. The process for producing a fluorinated methyl-benzyl alcohol according to claim 6, wherein the catalyst is a sponge cobalt catalyst or a modified sponge cobalt catalyst.

9. The process for producing a fluorinated methyl-benzyl alcohol according to claim 6, wherein the catalyst is a supported cobalt catalyst, a supported nickel catalyst, a supported palladium catalyst or a supported rhenium catalyst.

10. The process for producing a fluorinated methyl-benzyl alcohol according to claim 5, wherein the solvent is a single or mixed solvent comprising at least one selected from saturated aliphatic or alicyclic hydrocarbon, aromatic hydrocarbon, alcoholic solvent, ether of aliphatic or alicyclic hydrocarbon and water.

11. The process for producing a fluorinated methyl-benzyl alcohol according to claim 10, wherein the solvent is a single or mixed solvent comprising at least one selected from toluene, xylene, methanol, ethanol, dioxane, dioxolane and water.

12. The process for producing a fluorinated methyl-benzyl alcohol according to claim 1, wherein the hydrogenolysis reaction is carried out in a hydrogen partial pressure of from 0.05 to 15 MPa.

13. The process for producing a fluorinated methyl-benzyl alcohol according to claim 5, wherein the amount of the solvent used in the hydrogenolysis reaction is 1 to 20 times by mass based on the fluorinated benzene dimethanol.

14. The process for producing a fluorinated methyl-benzyl alcohol according to claim 1, wherein hydrogenolysis is carried out using hydrogen in an amount of 100 to 180% by mole based on the fluorinated benzene dimethanol.

* * * * *